US009349494B2

(12) United States Patent
Roessl

(10) Patent No.: US 9,349,494 B2
(45) Date of Patent: May 24, 2016

(54) X-RAY BEAM SHAPER

(71) Applicant: KONINKLIJKE PHILIPS N.V., Eindhoven (NL)

(72) Inventor: Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 96 days.

(21) Appl. No.: 14/381,234

(22) PCT Filed: Feb. 6, 2013

(86) PCT No.: PCT/IB2013/050975
§ 371 (c)(1),
(2) Date: Aug. 27, 2014

(87) PCT Pub. No.: WO2013/132361
PCT Pub. Date: Sep. 12, 2013

(65) Prior Publication Data
US 2015/0092917 A1 Apr. 2, 2015

Related U.S. Application Data

(60) Provisional application No. 61/607,805, filed on Mar. 7, 2012.

(51) Int. Cl.
*G01N 23/04* (2006.01)
*G21K 1/02* (2006.01)
*A61B 6/03* (2006.01)
*A61B 6/06* (2006.01)
*A61B 6/00* (2006.01)

(52) U.S. Cl.
CPC . *G21K 1/02* (2013.01); *A61B 6/032* (2013.01); *A61B 6/06* (2013.01); *A61B 6/4021* (2013.01); *A61B 6/4035* (2013.01); *G01N 23/04* (2013.01)

(58) Field of Classification Search
CPC ........... G21K 1/02; G01N 23/04; A61B 6/06; A61B 6/032; A61B 6/4021; A61B 6/4035
USPC ................................ 378/4–20, 145–155, 156
See application file for complete search history.

(56) References Cited

U.S. PATENT DOCUMENTS

| 6,385,278 B1 * | 5/2002 | Hsieh ..................... A61B 6/032 378/15 |
|---|---|---|
| 2003/0198319 A1 | 10/2003 | Toth et al. |
| 2004/0234037 A1 * | 11/2004 | Hoffman ................ A61B 6/032 378/156 |
| 2005/0089146 A1 | 4/2005 | Toth et al. |
| 2009/0262997 A1 | 10/2009 | Zou et al. |
| 2010/0254585 A1 | 10/2010 | Brunner et al. |

FOREIGN PATENT DOCUMENTS

| JP | 2010082031 A | 4/2010 |
|---|---|---|
| WO | 2005036467 A1 | 4/2005 |
| WO | 2007069121 A1 | 6/2007 |

* cited by examiner

*Primary Examiner* — Courtney Thomas

(57) ABSTRACT

An imaging system (500) includes a focal spot (508) that rotates along a path around an examination region and emits a radiation beam that traverses a field of view of the examination region and a subject or object therein. The system further includes a detector array (520) that is located opposite the radiation source, across the examination region. The detector array detects radiation traversing the field of view and outputs a signal indicative of the detected radiation. The system further includes a beam shaper that is located between the radiation source and the examination region. The beam shaper rotates with the focal spot and, relative to the focal spot, in an opposite direction of the focal spot with a same angular frequency as the rotating of the focal spot and attenuates the radiation beam which reduces a flux density across the detector array at each rotational angle of the focal spot.

19 Claims, 7 Drawing Sheets

Figure 5:
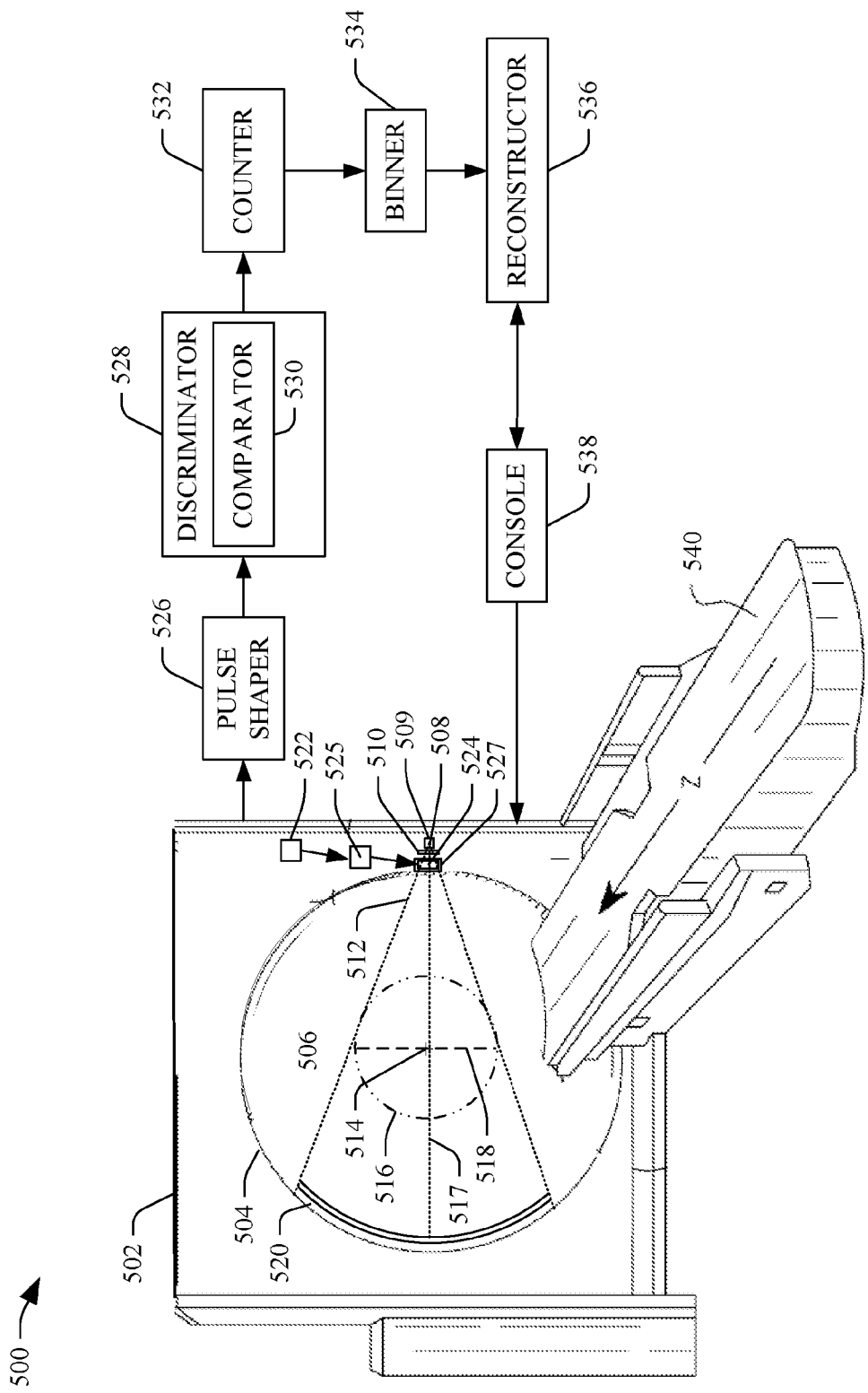

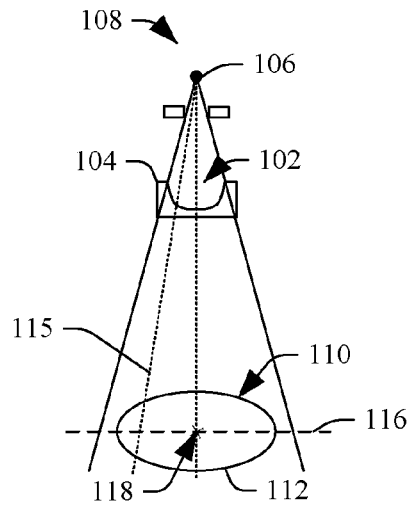
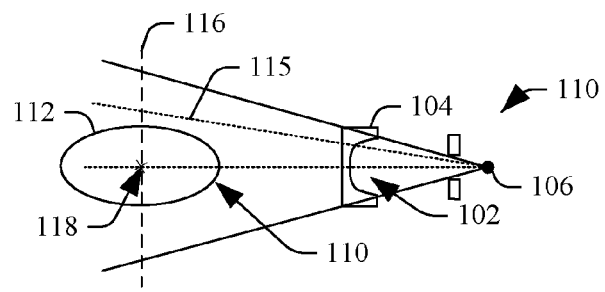
FIGURE 1
(PRIOR ART)
FIGURE 2
(PRIOR ART)
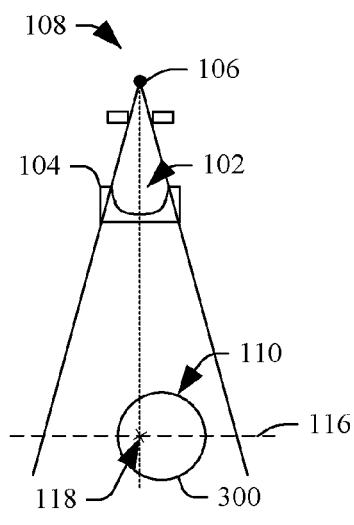
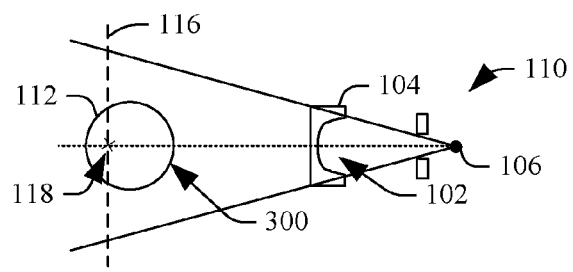
FIGURE 3
(PRIOR ART)
FIGURE 4
(PRIOR ART)

X-RAY BEAM SHAPER

CROSS REFERENCE TO RELATED APPLICATIONS

This application is a national filing of PCT application Serial No. PCT/IB2013/050975, filed Feb. 6, 2013, published as WO 2013/132361 A2 on Sep. 2, 2013, which claims the benefit of U.S. provisional application Ser. No. 61/607,805 filed Mar. 7, 2012, which is incorporated herein by reference.

The following generally relates to computed tomography (CT) and more particular to a pre-subject/object x-ray beam shaper.

A CT scanner includes an x-ray tube that emits an x-ray beam. A first portion of the x-ray beam traverses a subject or object located in a field of view of an examination region and is attenuated as a function of the radiodensity of the subject or object. A second portion of the x-ray beam traverses the field of view of the examination region without traversing the subject or object. A detector array, disposed across the examination region from the x-ray tube, detects the radiation traversing the field of view and produces a signal indicative thereof. A reconstructor reconstructs the signal, producing volumetric image data.

A beam shaper has been positioned in the path of the x-ray beam between the x-ray tube and the examination region. The beam shaper is shaped so as to attenuate the beam to a greater degree at a periphery of the beam. The beam shaper has been referred to as a bowtie filter as its general physical shape resembles a bowtie. The beam shaper has been used to reduce the dynamic range requirements of a detector, for example, in a scanner with a detector having limited dynamic range, such as gas (e.g., Xenon) detector. The beam shaper has also been used to reduce patient dose and beam hardening artifacts with scintillator/photosensor detectors.

This beam shaper is also well-suited for reducing the flux in connection with direct conversion photon counting detectors, which, like gas detectors, have limited dynamic range and which also suffer from insufficient count rate capabilities at the higher flux rates of CT. That is, in a typical CT scan, excessive count rates are required for rays of the beam that do not traverse the subject or object, for example, rays at the periphery of the beam, or rays of the beam that traverse only a short distance through the subject or object, for example, that traverse at or near the periphery of the subject or object and are attenuated less than a particular amount.

However, such a beam shaper, in its current implementation, has limited performance, for example, because the profile of the beam shaper does not correspond to a profile of a subject in the field of view over the entire angular range required for a scan (i.e., at least 180 degrees plus a fan angle). This is shown in FIGS. 1 and 2 where a profile 102 of a beam shaper 104, relative to a focal spot 106, remains the same as the focal spot 106 rotates from a first rotational angle 108 (FIG. 1) to a second rotational angle 110 (FIG. 2), whereas a profile 110 of a generally elliptical shaped patient 112 located at iso-center, relative to the focal spot 106, changes.

In FIGS. 1 and 2, the beam shaper 104 has a profile that corresponds to the orientation of the patient shown in FIG. 1 with the long axis of the patient 112 generally parallel to the beam shaper 104. With this profile, in FIG. 1, the thickness of the beam shaper 104 traversed by the ray 115 corresponds to the thickness of the patient 112 traversed by the ray 115. In FIG. 2, the ray 115 traverses the same thickness of the beam shaper 104 as in FIG. 1 but the ray 115 does not traverse any patient. As a consequence, the intensity of the ray 115 is higher than desired at the second rotational angle 110 of FIG. 2.

A similar situation occurs where a subject 300 is positioned off-center, shifted from the iso-center 118, as shown in FIGS. 3 and 4, where the profile 102 of the shaper 104 does not correspond to the profile 110 of the off-centered subject 300 at any angle and changes from angle to angle. As a consequence of at least one of the above noted shortcomings, even though the beam shaper 104 reduces the flux where the rays do not traverse the subject 112 or 300, the beam shaper 104 may cause deviations from the desired homogenous (constant) illumination of the detector array as a function of the angular position of the beam shaper 104, which can degrade image quality.

Aspects described herein address the above-referenced problems and others.

In one aspect, an imaging system includes a focal spot (508) that rotates along a path around an examination region and emits a radiation beam that traverses a field of view of the examination region and a subject or object therein. The system further includes a photon counting detector array that is located opposite the radiation source, across the examination region. The detector array detects radiation traversing the field of view and outputs a signal indicative of the detected radiation. The system further includes a beam shaper that is located between the radiation source and the examination region. The beam shaper rotates with the focal spot and, relative to the focal spot, in an opposite direction of the focal spot with a same angular frequency as the rotating of the focal spot and attenuates the radiation beam which reduces a flux density across the detector array at each rotational angle of the focal spot.

In another aspect, a method includes rotating a focal spot and a beam shaper, together, through a predetermined angular range on a path around an examination region and a subject or object therein at a given angular frequency during a scan of the subject or object in a first direction, concurrently, rotating the beam shaper in a direction opposite of the first direction, relative to the focal spot, at the same given angular frequency, and concurrently, detecting radiation emitted by the focal spot that traverses the beam shaper, a field of view, and the subject or object, and strikes a detector located opposite the focal spot, and generating an output signal indicative thereof.

In another aspect, a beam shaper of an imaging system includes an outer perimeter and an inner perimeter. The inner perimeter defines at least one material free region there through and corresponds to a profile of a model of a cross section of a human subject in the field of view. An x-ray attenuating material is between the outer and inner perimeters.

The invention may take form in various components and arrangements of components, and in various steps and arrangements of steps. The drawings are only for purposes of illustrating the preferred embodiments and are not to be construed as limiting the invention.

FIG. 1 schematically illustrates an example prior art bowtie shaped beam shaper at a first angle in connection with an elliptical shaped subject or object centered about iso-center.

FIG. 2 schematically illustrates the example prior art bowtie shaped beam shaper of FIG. 1 at a second different angle in connection with the elliptical shaped subject or object centered about iso-center.

FIG. 3 schematically illustrates the example prior art bowtie shaped beam shaper of FIG. 1 at the first angle in connection with an off-centered subject or object.

FIG. 4 schematically illustrates the example prior art bowtie shaped beam shaper of FIG. 1 at a second different angle in connection with the off-centered subject or object.

FIG. 5 schematically illustrates an example imaging system that includes at least one beam shaper that provides angular independent homogenization of the x-ray flux detected by the detector array of the imaging system.

Figure 6:
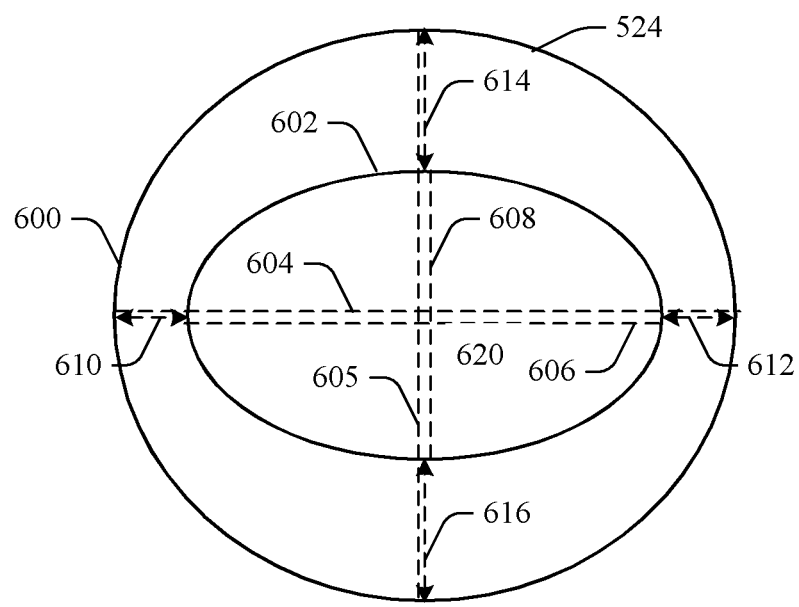

FIG. 6 schematically illustrates an example of the at least one beam shaper.

Figure 7:
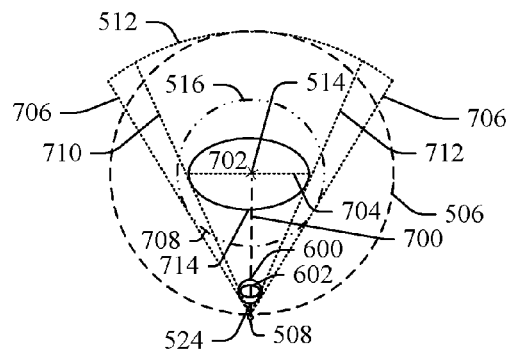

FIG. 7 schematically illustrates the example beam shaper of FIG. 6 with respect to at first angular location during a scan.

Figure 8:
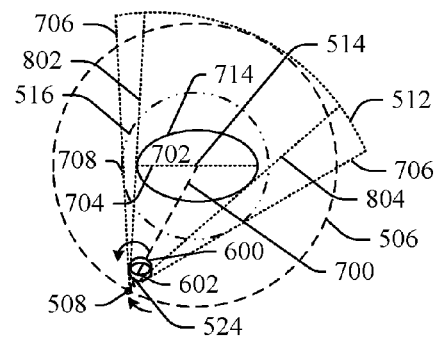

FIG. 8 schematically illustrates the example beam shaper of FIG. 6 with respect to second angular location during a scan.

Figure 9:
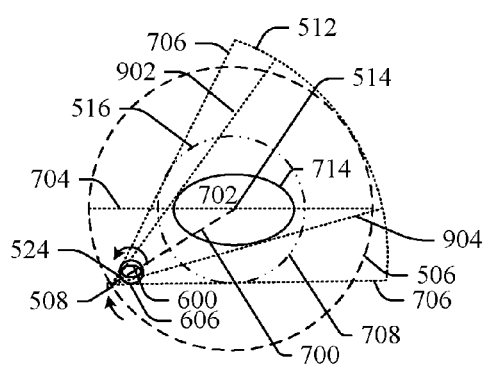

FIG. 9 schematically illustrates the example beam shaper of FIG. 6 with respect to third angular location during a scan.

Figure 10:
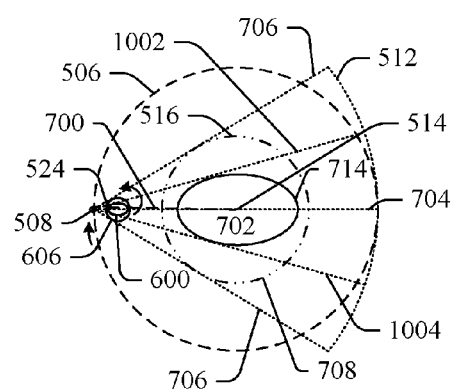

FIG. 10 schematically illustrates the example beam shaper of FIG. 6 with respect to fourth angular location during a scan.

Figure 11:
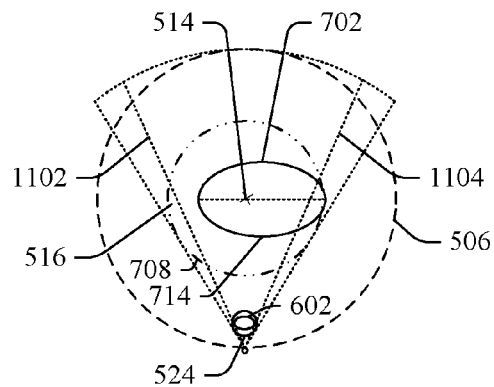
Figure 12:
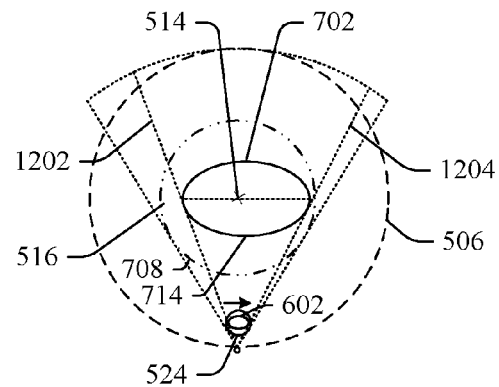

FIGS. 11 and 12 schematically illustrate an example in which the beam shaper is circumferentially translated to compensate for an off center subject or object.

Figure 13:
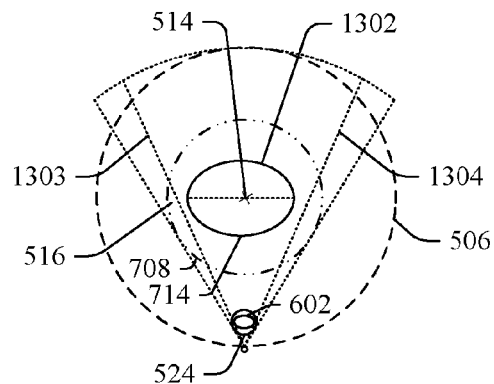
Figure 14:
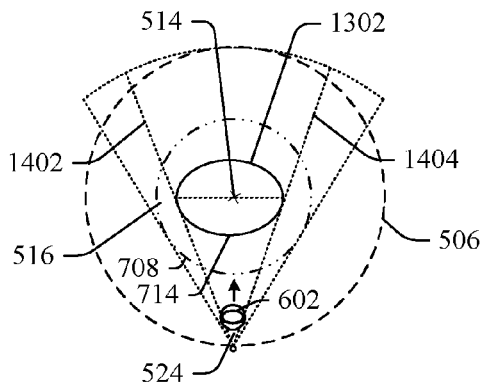

FIGS. 13 and 14 schematically illustrate an example in which the beam shaper is radially translated to compensate for smaller subject or object.

Figure 15:
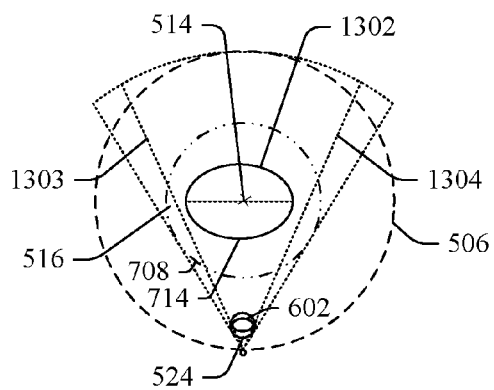
Figure 16:
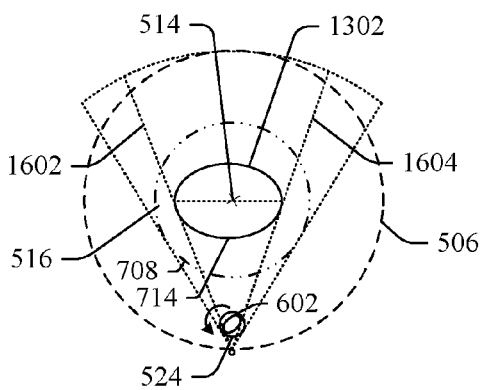

FIGS. 15 and 16 schematically illustrate an example in which the beam shaper is rotated to compensate for smaller subject or object.

Figure 17:
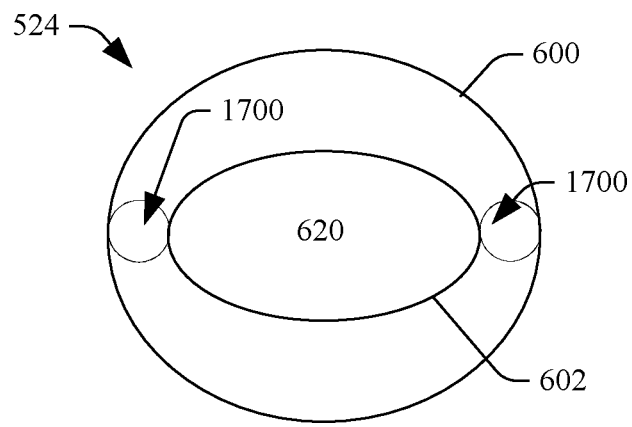

FIG. 17 schematically illustrates a variation of the beam shaper in which the beam shaper takes into account the arms of a subject along with the shoulders of a subject.

Figure 18:
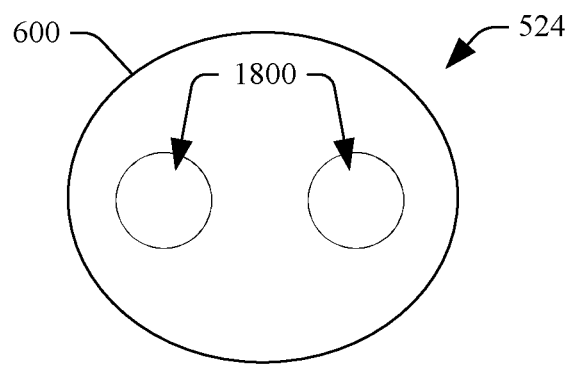

FIG. 18 schematically illustrates a variation of the beam shaper in which the beam shaper takes into account the lower extremities of a subject.

Figure 19:
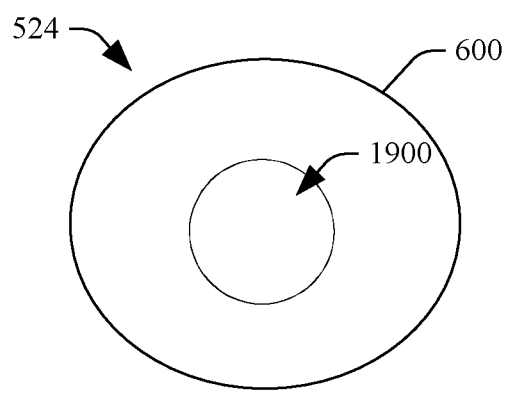

FIG. 19 schematically illustrates a variation of the beam shaper in which the beam shaper takes into account the head of a subject.

Figure 20:
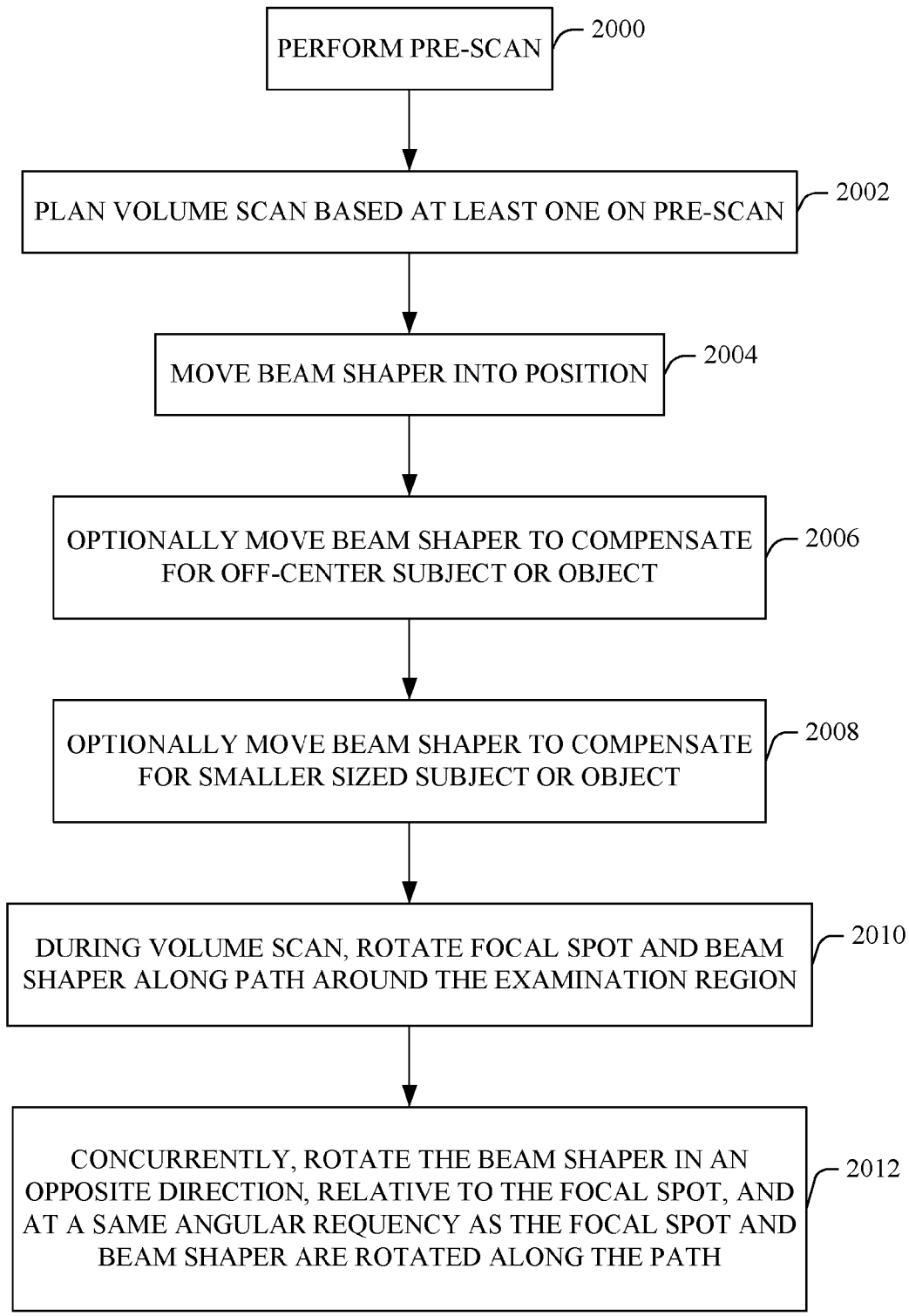

FIG. 20 illustrates a method.

FIG. 5 illustrates an imaging system 500 such as a computed tomography (CT) scanner. The imaging system 500 includes a stationary gantry 502 and a rotating gantry 504, which is rotatably supported by the stationary gantry 502. The rotating gantry 504 rotates around an examination region 506, about a longitudinal or z-axis.

A radiation source 509, such as an x-ray tube, is supported by the rotating gantry 504 and rotates with the rotating gantry 504 about the examination region 506, and emits radiation, via a focal spot 508, that traverses the examination region 506. A source collimator 510 is disposed between the radiation source 509 and the examination region 506 and collimates the emitted radiation to produce a generally fan or, wedge, cone, or otherwise shaped x-ray beam 512. The beam 512 is centered about an iso-center 514 of the examination region 506 and defines a generally circular shaped field of view 516 to reconstruct for a transverse reconstruction plane 518, which is generally perpendicular to a center ray 517 of the beam 512 and which extends through the iso-center 514.

A radiation sensitive detector array 520 is located opposite the radiation source 509, across the examination region 506. The detector array 520 includes one or more rows of photon counting detector pixels, such as direct conversion photon counting detector pixels, that detect radiation traversing the examination region 506 and generate a signal indicative of the detected radiation. Generally, the signal includes an electrical current or voltage signal having a peak amplitude or height that is indicative of the energy of a detected radiation. The direct conversion photon counting detector pixels may include any suitable direct conversion material such as CdTe, CdZnTe, Si, Ge, GaAs or other direct conversion material. In another embodiment, the radiation sensitive detector array 520 instead includes one or more rows of integrating detectors, such as scintillator/photosensor and/or other detectors.

At least one beam shaper 524 is located between the collimator 510 and the examination region 506 in the path of the beam 512. The beam shaper 524 is a physical device that attenuates the beam. As described in greater detail below, in one instance, the beam shaper 524 attenuates the beam 512 to achieve an approximately same predetermined x-ray flux profile across the detector pixels of the detector array 520 at each angle of rotation. This allows for compensating for no or low attenuation at peripheral regions of the scanned subject or object (or high flux regions) while providing angular independent homogenization of the x-ray flux detected by the detector pixels.

A support 527 supports the beam shaper 524 in the system 500. The support 527 can be configured to support the beam shaper 524 to allow for independent rotational and/or translational motion (in one or more directions) of the beam shaper 524 relative to the focal spot 508, along with rotating the focal spot 508 and beam shaper 524 in coordination along a path around the examination region 506. One more controllers 522 and/or one or more drive systems 525 (e.g., a motor, a coupling, etc.) can be used to rotate and/or translate the beam shaper 524.

A pulse shaper 526 processes the electrical signal output by the detector array 520 and generates a pulse such as voltage or other pulse indicative of the energy of the detected photon. An energy discriminator 528 energy discriminates the pulse. In the illustrated example, the energy discriminator 528 includes at least one comparator 530, which compares the amplitude of the pulse with at least one energy threshold that corresponds to an energy of interest. The comparator 530 produces an output signal indicative of whether the energy of a detected photon is above or below the threshold.

A counter 532 increments (or decrements) a count value for each threshold. For instance, when the output of the comparator 530 for a particular threshold indicates that the amplitude of the pulse exceeds the corresponding threshold, the count value for that threshold is incremented. An energy binner 534 assigns the counted pulses to energy bins, which correspond to different energy ranges. For example, a bin may be defined for the energy range between two thresholds, where a photon resulting in a count for the lower threshold but not for higher threshold would be assigned to that bin.

Where the system 500 includes one or more rows of integrating detectors, the pulse shaper 526, the energy discriminator 528, the comparator 530, the counter 532, and the energy binner 534 can be omitted. In this instance, the beam shaper 524 is used to reduce patient dose and/or beam hardening artifacts.

A reconstructor 536 reconstructs the binned data using a spectral and/or conventional reconstruction algorithm and generates spectral and/or conventional volumetric image data indicative of the examination region and the portion of the subject or object therein. A subject support 540, such as a couch, supports a subject or object in the examination region 506 and can be used to position the subject or object with respect to x, y, and/or z axes before, during and/or after scanning.

A general purpose computing system serves as an operator console 538, and includes an output device such as a display and an input device such as a keyboard, mouse, and/or the like. Software resident on the console 538 allows the operator to control the operation of the system 500, for example, allowing the operator to select a particular beam shaper 524, a motion of the beam shaper 524, etc. directly or indirectly through selecting a pre-generated imaging protocol.

FIG. 6 illustrates a non-limiting example of the beam shaper 524.

The example beam shaper 524 is ring shaped with an outer elliptical perimeter 600 and an inner elliptical perimeter 602. The outer elliptical perimeter 600 has a major axis 604 and a minor axis 605, which is smaller than the major axis 604. The inner elliptical perimeter 602 has a major axis 606 and a minor axis 608, which is smaller than the major axis 606, forming an elliptical shaped material free region 620 through the beam shaper 524 that is surrounded in at least two dimensions by the beam shaper 524. Note that in FIG. 6 the axes 604, 605, 606 and 608 are shown offset form the center of the ellipses only so that they can be visually differentiated from each other. The beam shaper 524 has first and second thicknesses 610 and 612 along the major axis 606 and third and fourth thicknesses 614 and 616 along the minor axis 608, where the third and fourth thicknesses 614 and 616 are greater than the first and second thicknesses 610 and 612.

The beam shaper 524 can include one or more materials with suitable x-ray attenuation properties, for example, attenuation properties similar to the attenuation properties of water or near water, which has an attenuation property similar to the attenuation properties of soft tissue, attenuation properties similar to the attenuation of soft tissue, or other desired attenuation properties. An example of a suitable material with attenuation properties near water includes Polytetrafluoroethylene (PTFE), which is a synthetic fluoropolymer of tetrafluoroethylene. An example of a suitable Polytetrafluoroethylene is Teflon™, which is a product of E. I. du Pont de Nemours and Company (or DuPont), which is a company headquartered in Delaware, U.S. Other materials with an x-ray attenuation property near the attenuation property of a material of interest are also contemplated herein.

In the illustrated embodiment, the major and minor axes 606 and 608 are such that the inner perimeter 602 mimics the general elliptical shape of a human patient at the shoulders, and the major and minor axes 604 and 605 of the outer perimeter 600 are such the rays traversing a subject are suitably attenuated to reduce the flux below a predetermined threshold value but not over attenuated. A circular outer perimeter may result in over attenuating outer peripheral rays traversing the subject, which may result in a non-uniform noise distribution across the detector array 520.

Theoretically, the size and attenuation of the beam shaper 524 scales with its location between the focal spot 508 and the iso-center 514. For example, if the beam shaper 524 were moved from the iso-center 514 to half way between the focal spot 508 and the iso-center 514, the size of the beam shaper 524 would have to be reduced by a factor of two (2) and the attenuation of the beam shaper 524 would have to be doubled to achieve the same results. Generally, the size scaling factor is proportional to the displacement of the beam shaper 524 towards the focal spot 508 and the attenuation scaling factor is inversely proportional to the size scaling factor.

FIGS. 7, 8, 9 and 10 show the beam shaper 524 of FIG. 6 in operation through various angles of rotation.

In these figures, the beam shaper 524 is centered with respect to a line 700 draw from the focal spot 508 to the iso-center 514 and is configured to rotate with the focal spot 508 along a path around the examination region 506 and, additionally, rotate independent of the focal spot 508 and concurrently therewith in the opposite direction and with a same angular frequency.

In this example, the drive system 525 may include a motor, a coupling between the motor and the beam shaper 524, and the rotational support 527 and/or other components that facilitate rotating the beam shaper 524 independently from the focal spot 508. Furthermore, an elliptical shaped subject or object 702 having a long axis 704 is located in the field of view 516 of the examination region 506, centered with respect to the line 700 draw from the focal spot 508 to the iso-center 514. The subject or object 702 can alternatively be circular or irregular shaped.

In FIG. 7, the focal spot 508 and the beam shaper 524 are located at the six o'clock position. The angular orientation of the beam shaper 524 is such that it corresponds to the orientation of the subject or object 702. As such, outer rays 706 of the beam 512 traverse along the outer perimeter 600 of the beam shaper 524 and an outer perimeter 708 of the field of view 516. Rays 710 and 712 of the beam 512 traverse along the inner perimeter 602 of the beam shaper 524 and along an outer perimeter 714 of the subject or object 702.

In FIG. 8, the focal spot 508 and the beam shaper 524 are rotated thirty-degrees clockwise around the examination region 506 with respect to the six o'clock position, and the beam shaper 524, relative to the focal spot 508, has concurrently rotated thirty-degrees counter-clockwise with a same angular frequency of the rotating focal spot 508, essentially cancelling the rotation of the beam shaper 524 such that the beam shaper 524 effectively translates on the path without rotating, dynamically varying the profile of the beam shaper 524 with respect to the focal spot 508 in coordination with the varying profile of the subject 702.

Similar to FIG. 7, the outer rays 706 of the beam 512 traverse along the outer perimeter 600 of the beam shaper 524 and the outer perimeter 708 of the field of view 516. Rays 802 and 804 of the beam 512 traverse along the inner perimeter 602 of the beam shaper 624 and along the outer perimeter 714 of the subject or object 702. Without the concurrent counter rotation of the beam shaper 524, the profile of the beam shaper 524 with respect to focal spot 508 would not vary in coordination with the varying profile of the subject 702, for example, similar to the beam shaper profiles shown in FIGS. 1-4, and the rays of the beam 512 that traverse along the inner perimeter 602 of the beam shaper 624 would not traverse along the outer perimeter 714 of the subject or object 702.

In FIG. 9, the focal spot 508 and the beam shaper 524 are rotated another thirty-degrees clockwise (for a total of sixty-degrees) around the examination region 506 with respect to the six o'clock position, and the beam shaper 524, relative to the focal spot 508, has concurrently rotated another thirty-degrees counter clockwise with the same angular frequency. Similar to FIG. 7, the outer rays 706 of the beam 512 traverse along the outer perimeter 600 of the beam shaper 524 and the outer perimeter 708 of the field of view 516. Rays 902 and 904 of the beam 512 traverse along the inner perimeter 602 of the beam shaper 524 and along the outer perimeter 714 of the subject or object 702.

In FIG. 10, the focal spot 508 and the beam shaper 524 are rotated another thirty-degrees clockwise (for a total of ninety-degrees) around the examination region 506 with respect to the six o'clock position, and the beam shaper 524, relative to the focal spot 508, has concurrently rotated another thirty-degrees counter clockwise with the same frequency. Similar to FIG. 7, the outer rays 706 of the beam 512 traverse along the outer perimeter 600 of the beam shaper 524 and the outer perimeter 708 of the field of view 516. Rays 1002 and 1004 of the beam 512 traverse along the inner perimeter 602 of the beam shaper 524 and along the outer perimeter 714 of the subject or object 702.

It is to be understood that the angular positions illustrated in FIGS. 7-10 are provided for explanatory purposes and other angles (including angles over 360 degrees) and/or other angular increments are contemplated herein. It is also to be understood that a typical patient generally will not be perfectly elliptical and that regardless of differences in the actual shape, the beam shaper 524 provides improved homogenous illumination of the detector pixels of the detector array 520 relative to the prior art bowtie filter shown in FIGS. 1-4.

That is, even if the beam shaper 524 does not perfectly match the profile of the subject 702, the profile of the beam shaper 524 with respect to the focal spot 508 still varies with the varying profile of the subject 702 through counter rotating the beam shaper 524 concurrently with rotating the focal spot 508 and beam shaper 524 along the path around the examination region 516. As such, the profile of the beam shaper 524 more closely matches the profile of the subject 702 at each angle of rotation relative to FIGS. 1-4, where the profile of the beam shaper is the same at all angles. This allows for reducing the dynamic range of the detector array 520 while maintaining a desired flux density across the detector pixels of the detector array 520 at each angle of rotation.

Variations are contemplated below.

In FIGS. 11 and 12, the beam shaper 524 is also moveable in a transverse direction. As such, the beam shaper 524 can be moved to compensate for a subject or object that is located off-center. FIG. 11 shows the subject or object 702 shifted off center with respect to the iso-center 514, and the beam shaper 524 centered with respect to the iso-center 514. Rays 1102 and 1104 of the beam 512 that traverse along the inner perimeter 602 of the beam shaper 524 do not traverse along the outer perimeter 714 of the subject or object 702.

FIG. 12 shows movement of the beam shaper 524 to move the beam shaper 524 to compensate for the off centered position of the subject or object 702. After such movement, the rays 1202 and 1204 traverse along both the inner perimeter 602 of the beam shaper 524 and the outer perimeter 714 of the subject or object 702. The amount of the displacement of the beam shaper 524 can be, for example, deduced prospectively from a survey scan or otherwise.

In FIGS. 13 and 14, the beam shaper 524 is also moveable in a direction between the focal spot 508 and the iso-center 514. As such, the beam shaper 524 can be moved to compensate for smaller subjects or objects. FIG. 13 shows a smaller subject or object 1302 centered with respect to the iso-center 514, and the beam shaper 524 centered with respect to the iso-center 514. Rays 1303 and 1304 of the beam 512 that traverse along the inner perimeter 602 of the beam shaper 624 do not traverse along the outer perimeter 714 of the smaller subject or object 1302.

FIG. 14 shows movement of the beam shaper 524 towards the iso-center 514 to compensate for the smaller subject or object 1302. After such movement, the rays 1402 and 1404 of the beam 512 that traverse along the inner perimeter 602 of the beam shaper 524 also traverse along the outer perimeter 714 of the subject or object 702. Likewise, the amount of the displacement of the beam shaper 524 can be, for example, deduced prospectively from a survey scan or otherwise. Scaling of the attenuation can be compensated for in software or ignored.

In FIGS. 15 and 16, the beam shaper 524 is rotated to compensate for the smaller subjects or object 1302. With respect to FIG. 15, as described in connection with FIG. 13, the rays 1303 and 1304 of the beam 512 that traverse along the inner perimeter 602 of the beam shaper 524 do not traverse along the outer perimeter 714 of the subject or object 1302.

FIG. 16 shows the beam shaper 524 rotated to compensate for the smaller subject or object 1302. After such movement, rays 1602 and 1604 of the beam 512 that traverse along the inner perimeter 602 of the beam shaper 524 also traverse along the outer perimeter 714 of the subject or object 1302. The amount of the rotation of the beam shaper 524 can be, for example, deduced prospectively from a survey scan or otherwise.

It is to be understood that one or more combinations of the rotational and/or translational movements depicted in FIGS. 5-16 is also contemplated herein.

In another variation, the beam shaper 524 can be held at a static position so as to mimic a traditional bowtie filter, such as the bowtie filter of FIGS. 1-4 and/or other bowtie filter.

In another variation, the beam shaper 524 can be first rotated and/or translated, and then held at a static position during scanning.

In another variation, the beam shaper 524 can be used in conjunction with traditional bowtie filter and/or other beam filter such as a pre-shaper or other beam filter. A pre-shaper located between the focal spot and the beam shaper can be used to attenuate the beam so the intensity of the beam at each pixel is the same, assuming a subject perfectly fills the entire field of view 516.

In FIG. 5-16, the beam shaper 524 shape generally corresponds to the elliptical cross-section along the shoulders of a subject. Other beam shapers 524 are contemplated herein. For example, FIG. 17 shows a beam shaper 524 that additionally includes two circular material free regions 1700 corresponding to the arms of the subject.

FIG. 18 shows a beam shaper 524 that only includes two circular material free regions 1800 corresponding to legs of the subject. FIG. 19 shows a variation in which the beam shaper 524 includes a single circular portion 1900 corresponding to the head of the subject. Other beam shapers 524 configured for other parts of the subject are also contemplated herein.

In another variation, the beam shaper 524 is in the form of a three dimensional structure, for example, with different regions of the beam shaper 524 corresponding to different regions (e.g., head, shoulders and arms, legs, etc.) of the subject. Such a beam shaper can be a single structure or a combination of stacked individual beam shapers 524, such as those shown in FIGS. 17-19 and/or other beam shapers 524. In this instance, the beam shaper 524 additionally translates along the z-axis during a helical scan so that the region of the beam shaper 524 in the path of the beam 524 at any given time corresponds to the region of the subject being scanned.

By way of non-limiting example, the beam shaper 524 can be a whole body flux compensator that consists of a hollow cylinder with the air cavity in the form of a human being. During a scan, the cylinder would counter rotate as described herein and translate along the z-axis during a helical scan to align the various section of the human-like air cavity to the corresponding portion of the patient. Misalignment of the patient with the iso-center can at least approximately be compensated by translation in the radial direction. Such a beam shaper 524 can be generic to all (e.g., based on age, etc.) or specific to the subject or object being scanned.

For a beam shaper 524 specific to the subject or object, the shape of the beam former 524 can be based on previous scans and/or other information, a beam shaper 524 can be tailored to a specific subject or object. In this instance, the beam shaper 524 is configured such that authorized personnel such as a clinician, a radiology technician, etc. can install the beam shaper 524 in a carrier of the system 500 configured to selectively load and unload beam shapers 524 for scanning or in a static shaper support in the path the beam will traverse. Alternatively, service, manufacturing, etc. can install the beam shaper 524.

Where the at least one beam shaper 524 includes multiple beam shapers, a given beam shaper can be alternately positioned in the path of the beam 512 or outside of the path of the beam 512. The different beam shapers may corresponds to different regions of a subject (e.g., the shoulders, the legs, the head, etc.), a same region but a different size subject (e.g., infant, pediatric, or adult), etc.

In another variation, the beam shaper 524 compensates for the subject or object as shown in FIG. 6 but does not fill the entire field of view. This may reduce the total diameter of the beam shaper 524.

FIG. 20 illustrates an example method in accordance with the embodiments described herein.

It is to be appreciated that the ordering of the acts in the methods described herein is not limiting. As such, other orderings are contemplated herein. In addition, one or more acts may be omitted and/or one or more additional acts may be included.

At 2000, a pre-scan of a subject or object is performed. The pre-scan can be a 2D projection scan such as a scout scan, a 3D low volume scan, and/or other scan.

At 2002, a volume scan of the subject or object is planned based on the pre-scan.

At 2004, a beam shaper of interest is moved into a beam path through a field of view, where the beam shaper is selectable. As described herein, a suitable beam shaper has a shape that corresponds to the field of view less a model of an average subject or object.

At 2006, optionally, where the subject or object is positioned off center with respect to the iso-center of the examination region, the beam shaper is moved to compensate for the off center positioning.

At 2008, optionally, where the size of the beam shaper does not correspond to the size of the subject or object, the beam shaper is moved to compensate for the size difference.

At 2010, during the volume scan, a focal spot and a beam shaper of an imaging system is rotated through a predetermined angular range on a path around an examination region at a given angular frequency during a scan of an elliptically shaped subject or object.

At 2012, concurrently with act 2000, the rotating beam shaper counter rotates relative to the focal spot over the predetermined angular range at the same angular frequency so that the beam shaper effectively translates along the path without rotating.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system, comprising:
   a focal spot configured to rotate along a path around an examination region and emit a radiation beam that traverses a field of view of the examination region;
   a detector array located opposite the focal point and across the examination region, the detector array configured to detect radiation traversing the field of view and output a signal indicative of the detected radiation; and
   a beam shaper located between the focal point and the examination region, the beam shaper configured to rotate with the focal spot and, relative to the focal spot, in an opposite direction of the focal spot with a same angular frequency as the rotating of the focal spot and attenuate the radiation beam which reduces a flux density across the detector array at each rotational angle of the focal spot.

2. The imaging system of claim 1, further comprising:
   a filter located between the focal spot and the beam shaper, wherein the filter attenuates the beam so that an intensity of the beam at each pixel is approximately the same.

3. The imaging system of claim 2, wherein the beam shaper includes an x-ray attenuating material that attenuates radiation traversing the field of view that does not traverse a subject or object disposed in the examination region.

4. The imaging system of claim 1, wherein the beam shaper has an elliptical shaped outer perimeter and an elliptical shaped inner perimeter that defines a material free region through the beam shaper and that corresponds to a cross sectional region along the shoulders, abdomen, and/or thorax of a human subject.

5. The imaging system of claim 4, further comprising:
   second and third material free regions corresponding to cross sectional regions of the arms of the human subject.

6. The imaging system of claim 1, wherein the beam shaper has an elliptical shaped outer perimeter and two circular shaped inner perimeter regions, each defining a material free region through the beam shaper and corresponding to a leg of a human subject.

7. The imaging system of claim 1, wherein the beam shaper has a first elliptical shaped outer perimeter and second circular shaped inner perimeter region that defines a material free region through the beam shaper and that corresponds to a head of a human subject.

8. The imaging system of claim 1, wherein the beam shaper is a three dimensional structure with different regions corresponding to different regions of a human subject.

9. The imaging system of claim 1, further comprising:
   a support that supports the beam shaper with respect to the focal spot and rotates along with the focal spot;
   a drive system that moves the beam shaper; and
   a controller that controls the drive system.

10. The imaging system of claim 9, wherein the support rotatably supports the beam shaper, and the controller controls the drive system to rotate the beam shaper with respect to the focal spot.

11. The imaging system of claim 9, wherein the support rotatably supports the beam shaper, and the controller controls the drive system to rotate the beam shaper to a predetermined rotational position and holds the beam shaper at that predetermined rotational position while rotating the rotating gantry.

12. The imaging system of claim 9, wherein the support supports the beam shaper for radial motion, and the controller controls the drive system to radially move the beam shaper for a scan.

13. The imaging system of claim 9, wherein the support supports the beam shaper for circumferential motion, and the controller controls the drive system to circumferential move the beam shaper for a scan.

14. A method, comprising:
rotating a focal spot and a beam shaper, together, through a predetermined angular range on a path around an examination region and a subject or object therein at a given angular frequency during a scan of the subject or object in a first direction;
concurrently, rotating the beam shaper in a direction opposite of the first direction, relative to the focal spot, at the same given angular frequency; and
concurrently, detecting radiation emitted by the focal spot that traverses the beam shaper, a field of view, and the subject or object, and strikes a detector located opposite the focal spot, and generating an output signal indicative thereof.

15. The method of claim 14, wherein the beam traversing the beam shaper and illuminating the detector array has a predetermined flux density profile across the detector array for each angular range for a plurality of different angular ranges.

16. The method of claim 15, further comprising:
pre-shaping the beam so that an intensity of the beam at each pixel is the same when scanning a subject or object that completely fills the field of view.

17. The method of claim 14, further comprising:
moving the beam shaper to align the beam shaper with an off center subject or object.

18. The method of claim 14, further comprising:
radially translating or rotating the beam shaper based on a size of the subject or object.

19. The method of claim 14, further comprising:
rotating the beam shaper to a predetermined angular position with respect to the focal spot; and
holding the beam shaper at the predetermined angular position while rotating the focal spot and the beam shaper, together, through the predetermined angular range on the path around the examination region.

* * * * *